United States Patent
Huber et al.

(10) Patent No.: US 7,720,613 B2
(45) Date of Patent: May 18, 2010

(54) METHOD FOR SEQUENCING NUCLEIC ACIDS

(75) Inventors: Christian Huber, Saarbrücken (DE); Herbert Oberacher, Saarbrücken (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 1163 days.

(21) Appl. No.: 10/490,074

(22) PCT Filed: Sep. 12, 2002

(86) PCT No.: PCT/EP02/10235

§ 371 (c)(1), (2), (4) Date: Mar. 17, 2004

(87) PCT Pub. No.: WO03/025219

PCT Pub. Date: Mar. 27, 2003

(65) Prior Publication Data

US 2004/0265826 A1    Dec. 30, 2004

(30) Foreign Application Priority Data

Sep. 14, 2001    (AT) .............................. A 1444/2001

(51) Int. Cl.
*G06F 19/00* (2006.01)
*G06G 7/58* (2006.01)
*G06F 7/76* (2006.01)

(52) U.S. Cl. ................................ 702/20; 702/19; 703/2

(58) Field of Classification Search ........................ None
See application file for complete search history.

(56) References Cited

U.S. PATENT DOCUMENTS 6,017,693 A * 1/2000 Yates et al. .................... 435/5

7,052,915 B2 * 5/2006 Aebersold et al. ............. 436/86

FOREIGN PATENT DOCUMENTS

| WO | WO 95/25281 A1 | 9/1995 |
| WO | WO 00/66771 A2 | 11/2000 |
| WO | WO 00/66771 A3 | 11/2000 |

OTHER PUBLICATIONS

Oberacher et al., Comparative Sequencing of Nucleic Acids by Liquid Chromatography—Tandem Mass Spectrometry, Anal. Chem., Web Release Date: Nov. 30, 2001, vol. 74, pp. 211-218.*
Little, D., et al., 1996, "Sequence Information for 42-108-mer DNAs (Complete for a 50-mer) by Tandem Mass Spectrometry", *J. Am Chem Soc*, 118:9352-9359.
Ni, J., et al., 1996, "Interpretation of Oligonucleotide Mass Spectra for Determination of Sequence Using Electrospray Ionization and Tandem Mass Spectrometry", *Analytical Chemistry*, 68(13):1989-1999.
Oberacher, H., et al., 2002, "Comparative Sequencing of Nucleic Acids by Liquid Chromatography—Tandem Mass Spectrometry", *Anal. Chem*. 74(1):211-218.
Rozenski, J., 2002, SOS: A Simple Interactive Program for ab initio Oligonucleotide Sequencing by Mass Spectrometry, *J Am Soc Mass Spectrom*, 2002(13):200-203.

* cited by examiner

*Primary Examiner*—Marjorie Moran
*Assistant Examiner*—Jason M Sims
(74) *Attorney, Agent, or Firm*—Charles N. Doyle; Olga Kay (57) ABSTRACT

Method for sequencing nucleic acids in which the values of the CID spectrum calculated for an assumed sequence are compared with the measured spectrum of the nucleic acid and the degree of correspondence is calculated, at least one position of the assumed sequence is modified and the degree of correspondence with the measured spectrum is recalculated.

2 Claims, 8 Drawing Sheets

SEQUENCE LISTING

<160> NUMBER OF SEQ ID NOS: 4

<210> SEQ ID NO 1
<211> LENGTH: 20
<212> TYPE: DNA
<213> ORGANISM: artificial
<220> FEATURE:
<223> OTHER INFORMATION: 20-mer oligonucleotide

<400> SEQUENCE: 1
gacaggaaag actttctggc                    20

<210> SEQ ID NO 2
<211> LENGTH: 20
<212> TYPE: DNA
<213> ORGANISM: artificial
<220> FEATURE:
<223> OTHER INFORMATION: reference 20-mer oligonucleotide -continued

```
<400> SEQUENCE: 2
gacaggaaag acattctggc                                               20

<210> SEQ ID NO 3
<211> LENGTH: 51
<212> TYPE: DNA
<213> ORGANISM: artificial
<220> FEATURE:
<223> OTHER INFORMATION: 51-mer oligonucleotide

<400> SEQUENCE: 3
aaaccacatt ctgagcatac ccccaaaaaa tttcatgccg aagctgtggt c             51

<210> SEQ ID NO 4
<211> LENGTH: 80
<212> TYPE: DNA
<213> ORGANISM: artificial
<220> FEATURE:
<223> OTHER INFORMATION: 80-mer oligonucleotide

<400> SEQUENCE: 4
ccccagtgct gcaatgatac cgcgagaccc acgctcaccg gctccagatt tatcagcaat    60
aaaccagcca gccggaaggg                                               80
```

METHOD FOR SEQUENCING NUCLEIC ACIDS

FIELD OF THE INVENTION

This application claims the benefit of priority under 35 U.S.C. §119 of PCT/EP2002/010235 filed 12 Sep. 2002 and AT Application A 1444/2001 filed 14 Sep. 2001, the contents of which are hereby incorporated by reference.

The invention concerns a method for sequencing nucleic acids in which the values of the CID spectrum calculated for an assumed sequence are compared with the measured spectrum of the nucleic acid and the degree of correspondence is calculated.

In such methods nucleic acids are firstly ionized, selected in a first spectrometer and then fragmented by collision with gaseous atoms or molecules (referred to as collision induced dissociation (CID)). The fragmentation conforms to known rules which is why the mass spectrographic examination of the fragments allows an inference to be made about the initial ion.

DESCRIPTION OF RELATED ART

When nucleic acids are fragmented, ions (a-B ions) are formed at the 5' end and at the 3' end (w ions). A method for completely elucidating the entire sequence starting from the ends is described in Ni, J.; Pomerantz, S. C.; Rozenski, J.; Zhang, Y.; McCloskey J. A. Anal. Chem. 1996, 68, 1989-99. Since an increasing number of insurmountable defects occur, this method is limited to nucleic acids of a small length (at most 15 mer). On the other hand a method of the type defined above is described in U.S. Pat. No. 6,017,693 (Yates et al) in which a library of peptides is examined with regard to whether they contain a compound corresponding to the measured spectrum. In this publication it is also suggested that the method be extended to oligonucleotides, but the method is typically restricted to 10 mers and below due to the enormous number of initial values that have to be examined.

SUMMARY OF INVENTION

The object of the invention is to make the known methods applicable to considerably longer sequences. This is essentially achieved in that the question that is asked is not primarily about the correct sequence but rather whether correspondence with the measured spectrum can be improved by systematically changing an initial sequence.

Hence the invention is characterized in that at least one position of the assumed sequence is modified and the degree of correspondence with the measured spectrum is recalculated.

Basically the invention allows an increasing approximation to the correct sequence starting with a random initial sequence that is assumed to be favourable by repeatedly applying the method. However, the actual strength of the method is in determining and locating point mutations and omissions or insertions of nucleic acid monomers in a known sequence. Particularly when the number of nucleotides is known, it is advantageous when each of the four possible nucleotides is used at a particular position and in each case the degree of correspondence with the spectrum is calculated. If this procedure is carried out for each position of the sequence and in each case the nucleotide having the best match is placed in the sequence, this finally results in an optimal match for the entire sequence.

Within the scope of the invention it is basically possible to use various methods to characterize the degree of correspondence between the calculated and measured spectrum by a numerical value. However, it is particularly simple when an algorithm is used to calculate the correspondence between the calculated and measured spectrum which is based on determining whether a measured value is present or not at the calculated position in the measured spectrum.

The m/z values for a certain fragment have to be calculated with high accuracy whereas the intensity of the measured values i.e. the frequency distribution of the various fragments is very difficult to predict. Hence it is appropriate to firstly refrain from predicting the intensities but rather to give the occurrence of a predicted measured value in the measured spectrum a higher rating when the measured intensity is higher. Since the m/z values have to be calculated with a higher degree of accuracy than their measurement, a difference value has to be defined up to which one regards a prediction as being fulfilled. This definition is based on the requirement that the number of false positives and false negatives has to be minimized.

Further details of the invention are discussed below on the basis of diagrams and embodiments.

DETAILED DESCRIPTION OF THE INVENTION

Principle of Sequencing by Means of Tandem Mass Spectrometry

Figure 1:
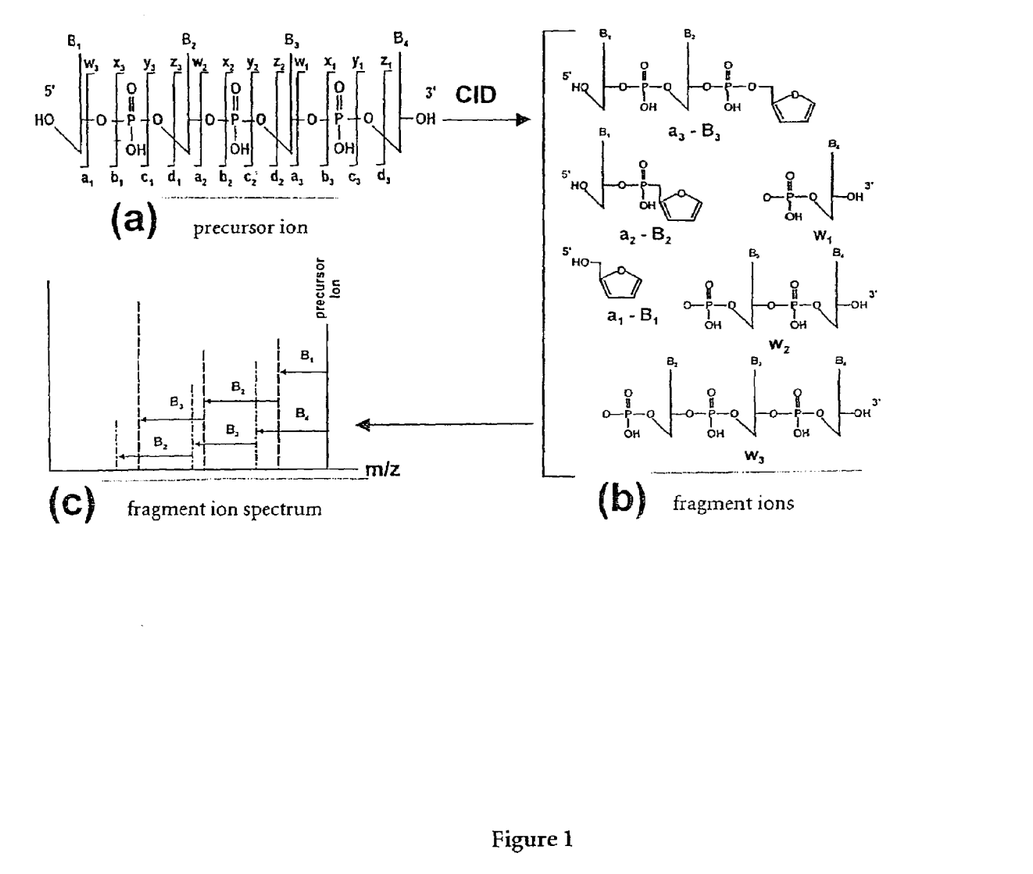
FIG. 1 elucidates the calculation of a fragmentation spectrum.

Nucleic acids are cleaved in a sequence-specific manner by collision-induced fragmentation whereby fragments of the precursor ion are formed which are designated according to the type of bond break in the phosphodiester group and the remaining charge. Whereas charge fragments having an intact 5'-terminal end are referred to as a, b, c, d fragments, charged fragments with an intact 3'-terminal end are referred to as w, x, y, z fragments (FIG. 1a). The number of deoxyribose residues of a fragment is denoted with subscript numbers and the charge state is denoted with superscript numbers. Thus $(a_5)^{2-}$ represents a fragment of the a series which consists of five nucleotide units and is twice negatively charged. Fragments in which a base has been additionally cleaved off are designated by adding —B e.g. as $(a_n\text{-}B_n)^{m-}$.

Although the fragmentation can basically occur at any bond, it has turned out that there is a main fragmentation path for oligonucleotide anions. In this process there is firstly a cleavage of the 3'-C—O bond of the sugar which subsequently leads to a loss of the base and formation of w and complementary (a-B) ions (FIG. 1b). Fragment ions of a particular type belong to a certain ion series where the mass differences within an ion series are determined by the masses of the bases in the sequence. Hence the sequence of a fragmented nucleic acid can be read off on the basis of the mass differences in an ion series (FIG. 1c).

Comparative Sequencing Strategy

The starting point of the sequencing approach according to the invention is the fact that a complete new determination of the sequence is not necessary for many genome-specific applications. It is usually sufficient to verify a sequence or to find small deviations from a known sequence. In this context sequencing by means of tandem mass spectrometry (MS/MS) is an attractive alternative to the sequencing method of Sanger that is conventionally used. The reason for this is that sequence-specific data can be obtained within seconds by collision-induced fragmentation and subsequent analysis of the fragment ions.

The closeness of correspondence between a measured MS/MS spectrum and a set of fragment ions which can be calculated on the basis of an assumed reference, can be described by almost any mathematic algorithm. An algorithm will be elucidated as an example in which the correspondence between the measured spectrum and the calculated fragment ions is characterized by the fitness value (FS). The fitness incorporates the absolute difference A between the measured and calculated m/z values, the relative intensity I % of the fragment ions, the number of assigned fragments K and the number of nucleotide positions M that are not covered by a fragment ion. The value for fitness becomes smaller with an increasing degree of correspondence between the measured spectrum and the calculated m/z values.

In order to find the sequence which matches best with the experimental data of an MS/MS spectrum, the first reference sequence is sequentially varied by incorporating all four possible nucleotides A, T, G and C at each position of the sequence. The sequence having the lowest fitness value is then identified as the correct sequence.

Development of the Sequencing Algorithm

Figure 2:
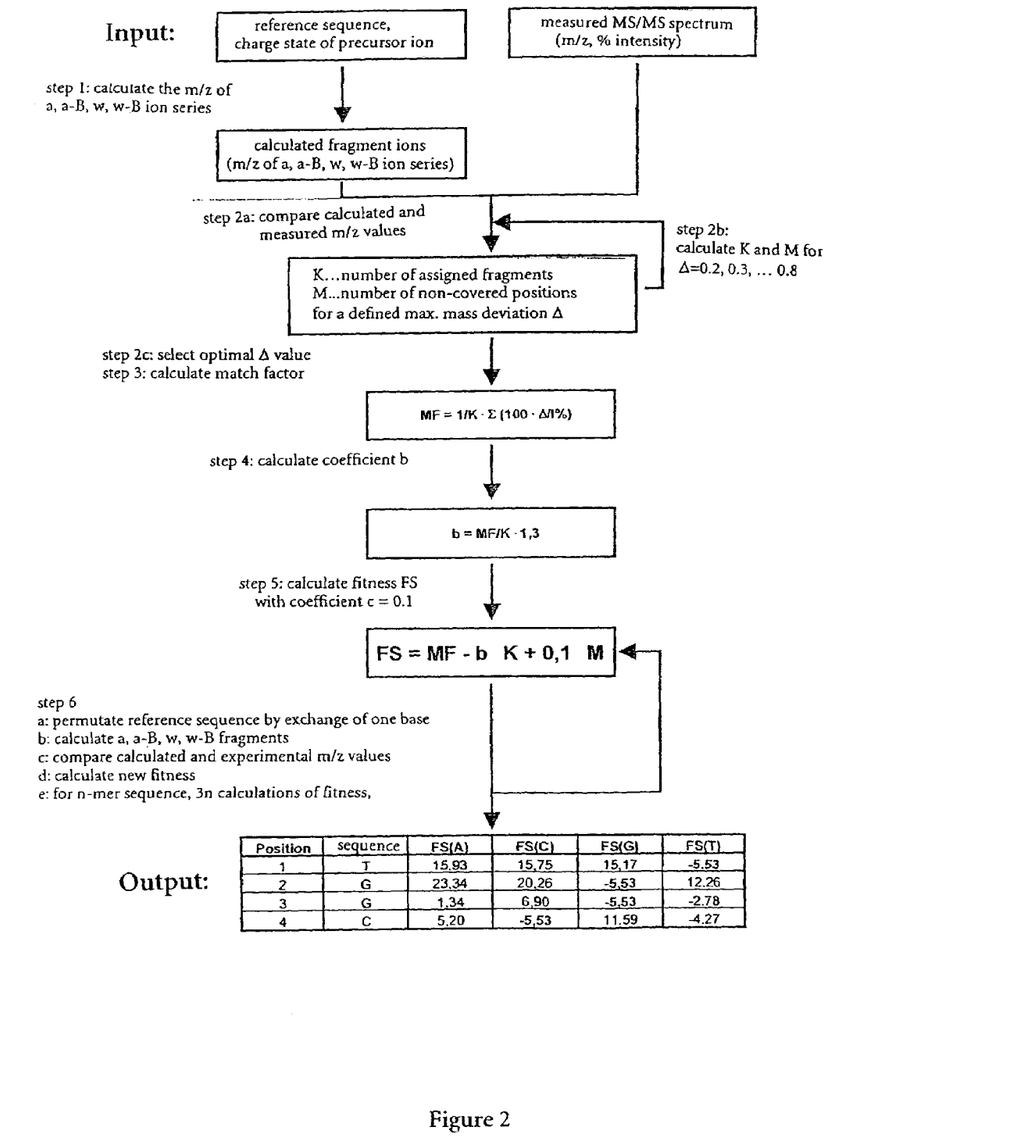
FIG. 2 concerns the procedure for comparing a calculated and a measured spectrum.
Figure 3:
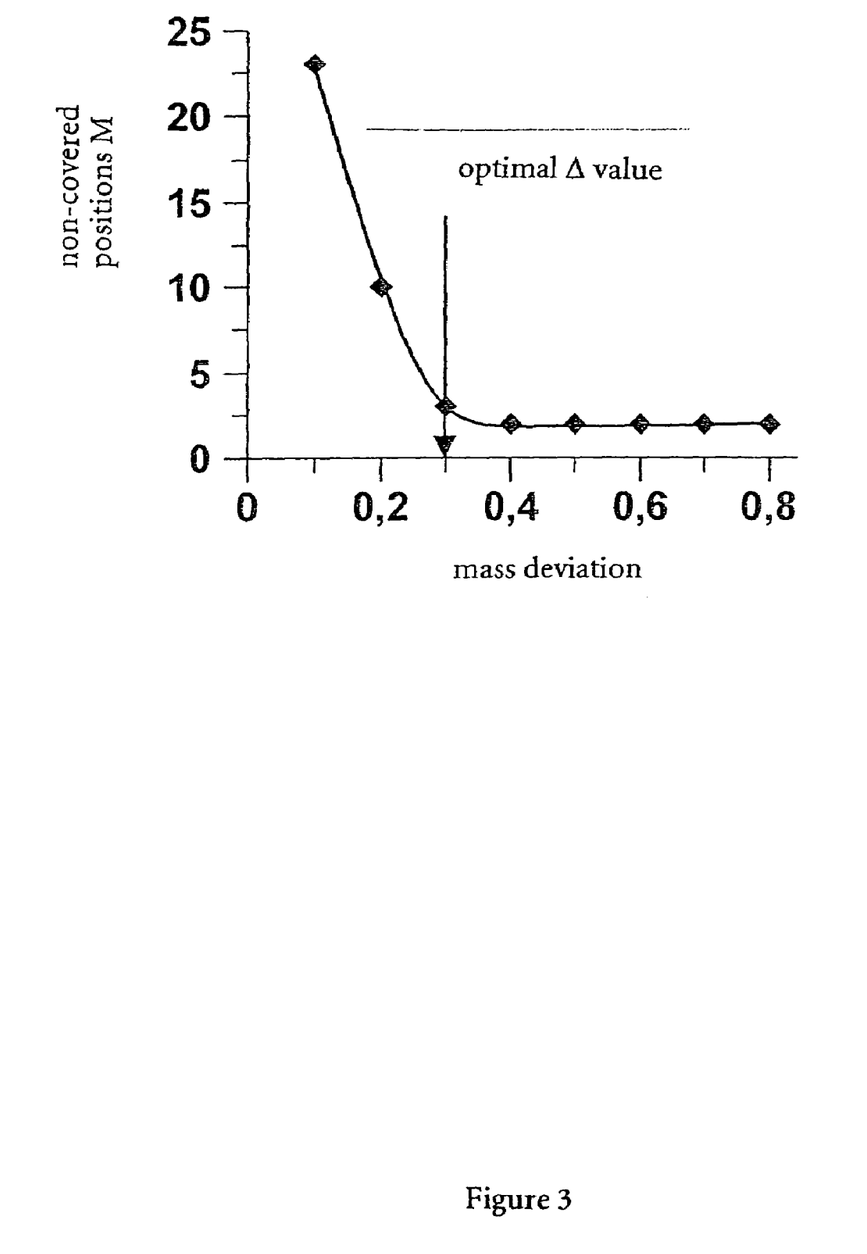
FIG. 3 relates to the optimization of the algorithm of FIG. 2.

FIG. 2 shows the procedure for the comparative sequencing of nucleic acids. The input parameters are the reference sequence together with the charge state of the precursor ion on the one hand, and a list of experimentally determined m/z values and their relative intensities I % on the other hand. A list of monoisotopic m/z values for the a, a-B, w and w-B ion series taking into consideration all possible charge states of the fragment ions from 1-up to the charge state of the precursor ion, is calculated from the reference sequence (step 1, FIG. 2). Subsequently the calculated m/z values and those found experimentally are compared (step 2a, FIG. 2). The result of this comparison is the number of fragment ions (K) that could be assigned a calculated m/z value and the sum of non-covered a and w positions (M). Non-covered a positions are those positions in the spectrum for which neither an a-B nor an a fragment of any possible charge state could be found. Similarly non-covered w positions are those positions in the spectrum for which neither a w-B nor a w fragment of any possible charge state could be assigned. In order to assign a fragment, the absolute value of the difference between the measured and the calculated m/z value must be smaller or equal to a tolerance value ($\Delta$). Values for K and M are calculated in increasing order for all $\Delta$ values between 0.2 and 0.8 in 0.1 steps (step 2b, FIG. 2). Subsequently the optimal $\Delta$ value is selected on the basis that the number of false-positive ($\Delta$ too large) and false-negative ($\Delta$ too small) assignments is minimized (step 2c, FIG. 2). The optimum $\Delta$ value can be deduced from a plot of M versus $\Delta$ as the $\Delta$ value just before the curve reaches a constant value (FIG. 3).

Figure 4:
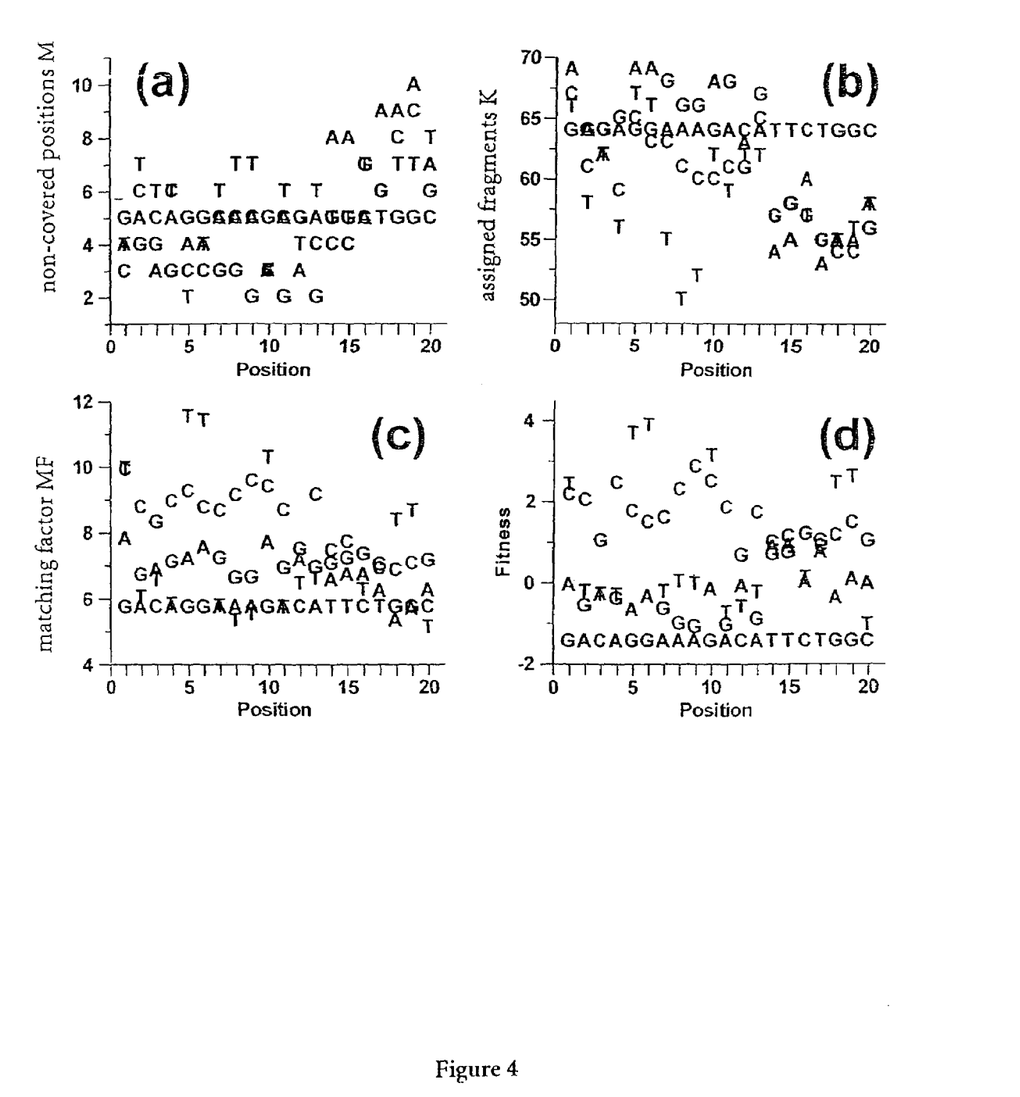
FIG. 4 shows the relative importance of the factors of the algorithm of FIG. 2.

The next step of the algorithm is to calculate a match factor MF which reflects the quality of the assignment of the m/z values in terms of mass deviation and intensity (step 3, FIG. 2). The match factor MF is defined as the sum of all quotients of the absolute mass deviation $\Delta$ and the intensity I (since the intensity is entered in %, the value is multiplied by 100) averaged over the total number of assignments K. This results in the following equation MF=1/K·$\Sigma$(100·$\Delta$/I %) (FIG. 2). The three parameters, the match factor MF, the number of assigned fragment ions K and sum of non-covered positions M are summarized by the following equation FS=a·MF−b·K+ c·M to describe the fitness of the sequence. The value for fitness becomes smaller with smaller mass differences, higher signal intensities, a larger number of assignments and lower sum of non-covered positions. As FIG. 4 clearly shows, the sequence can only be correctly verified by the interplay of the three individual terms of the equation (match factor MF, number of assigned fragment ions K and sum of non-covered positions M) (FIG. 4d). In contrast other sequences would have been assigned in each case as having a better fit with the MS/MS spectrum if the three individual terms were taken into consideration alone (FIG. 4a-c). Three coefficients a, b and c which weigh the terms of the equation were introduced to combine the match factor MF with the number of assigned fragment ions K and the sum of non-covered positions M. The value for the coefficient a is chosen as 1 by definition, whereas b and c are determined empirically. The coefficient b is selected in such a way that the ratio of the first and second terms of the equation MF:(b·K) is 1:1.3. Thus b=MF/K·1.3 (step 4, FIG. 2). A value of 0.1 for the coefficient c has been found to be appropriate for all examples described here. If the coefficients are inserted in the above equation one obtains for FS (step 5, FIG. 2):

$$FS = 1/K \cdot \Sigma \mid 100 \cdot \frac{\Delta}{I\ \%} \mid -b \cdot K + 0.1 \cdot M$$

The first calculated value for fitness is a measure of the correspondence of the measured MS/MS spectrum with the set of fragment ions calculated on the basis of the reference sequence. In order to find a sequence that may have a better correspondence or to confirm the identity of the measured sequence with the reference sequence, the reference sequence is systematically varied at every position and subsequently a new fitness is calculated for each of these mutated sequences. This is done by sequentially replacing the base at each position by the three other bases while the remainder of the sequence is kept constant (step 6a, FIG. 2). Assuming that the sequence contains only one mutation, 3n calculations of FS are carried out for a sequence of n nucleotides (step 6b-e, FIG. 2). In this connection it is important to note that the weight factor b is kept constant for all varied sequences and corresponds to the value (b=MF/K·1.3) calculated in step 4 of the algorithm from the number of assigned fragment ions K and the sum of non-covered positions (M) of the original reference sequence. The result of the overall calculation is a matrix which includes the fitness of the reference sequence (numbers printed in bold type, FIG. 2) and of the varied sequences at the various positions of the sequence (FIG. 2). For example the FS(T) value in line 1 of the matrix (−5.53) represents the fitness of the sequence TGGC. In contrast FS(A) is the value for the sequence in which the T at position 1 was replaced by an A (15.93). It can be seen that in this example the lowest FS value was obtained for the reference sequence leading to the conclusion that the best correspondence is between the experimental spectrum and the reference sequence. Substitution of a base would be indicated by an FS value for a mutated sequence that is smaller than the FS value of the reference sequence.

EXAMPLES

Example 1

Comparative Sequencing of a 20 mer oligodeoxynucleotide

Figure 5:
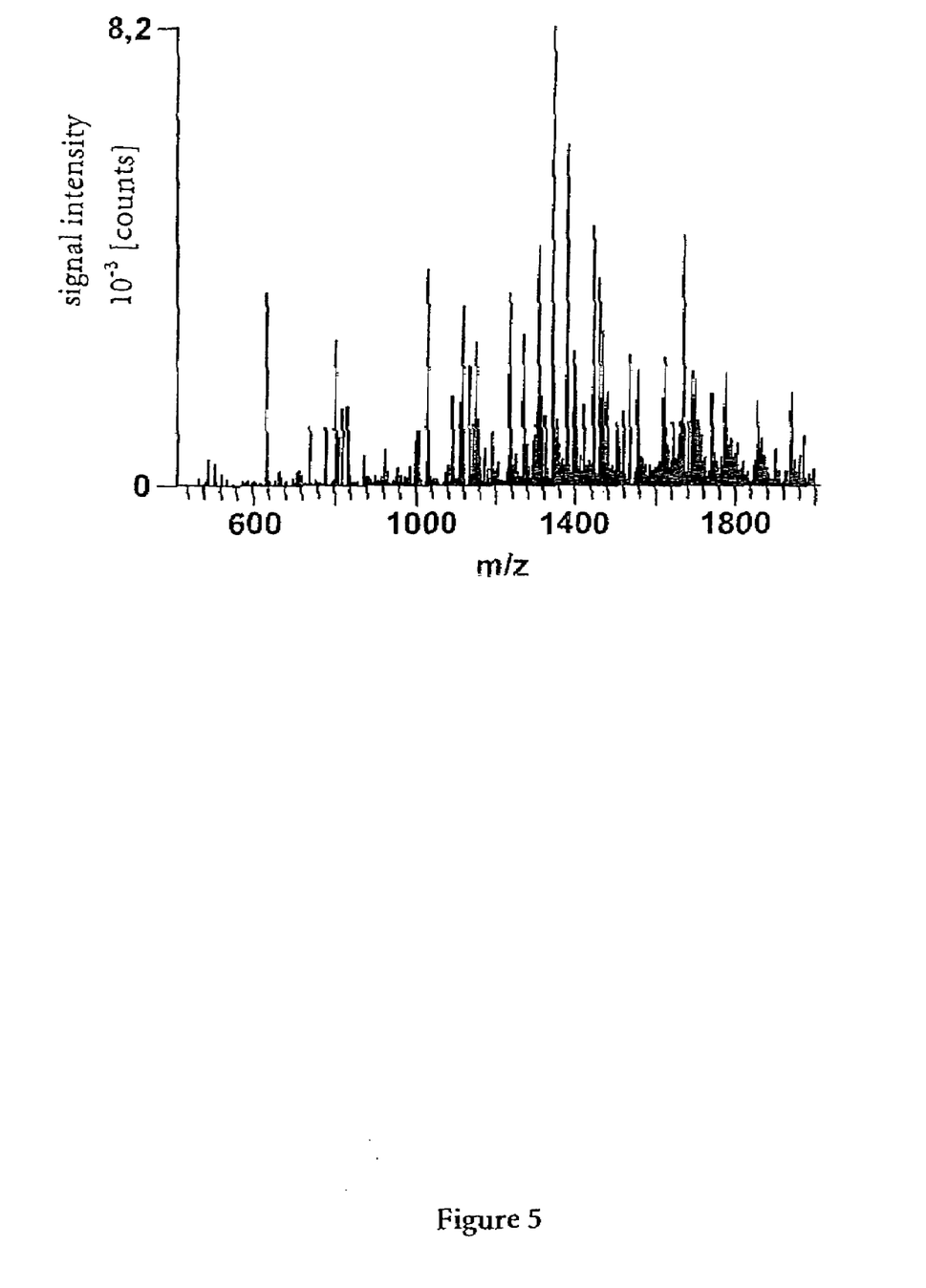
FIG. 5 is the measured spectrum of a 20 mer oligodeoxynucleotide.
Figure 6:
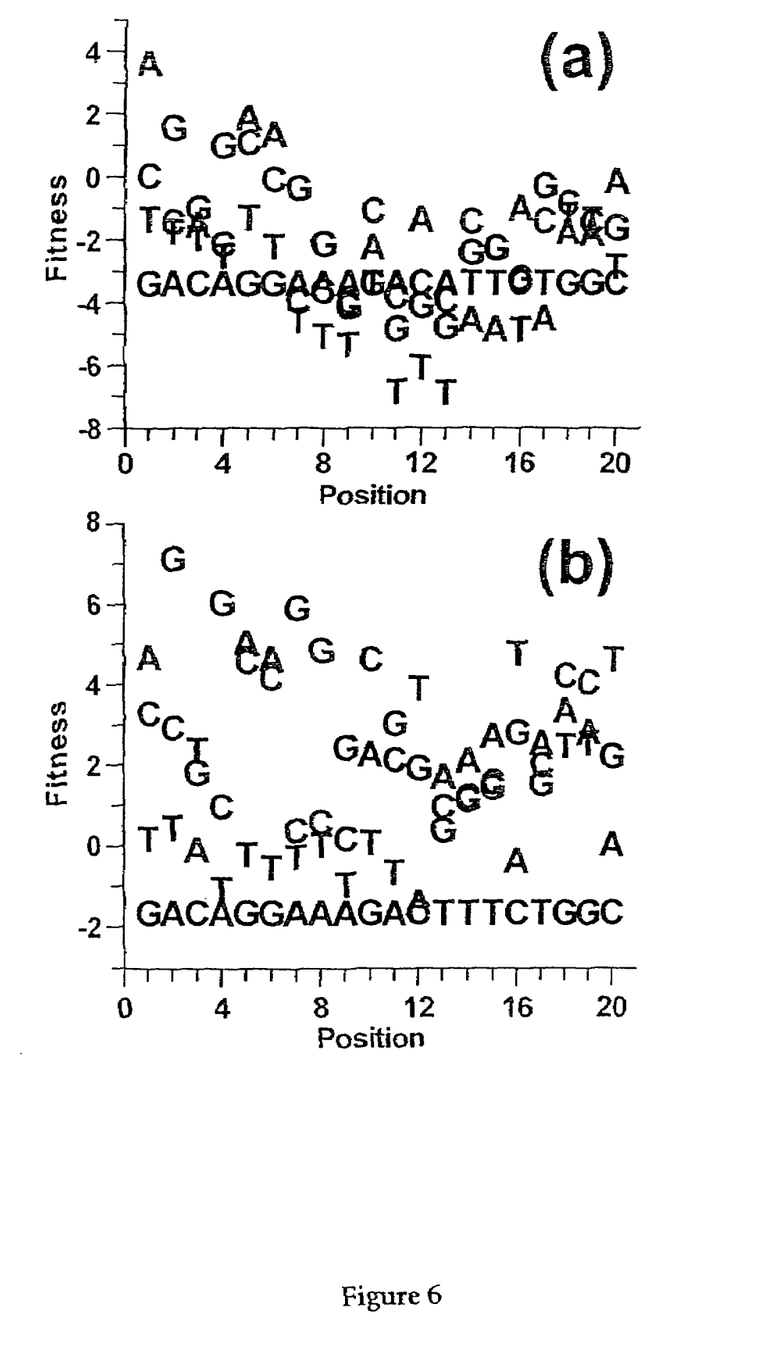
FIGS. 6a and 6b show the deduction of a sequence having a maximum correspondence with FIG. 5.

The MS/MS spectrum of a 20 mer having the sequence GACAGGAAAG ACTTTCTGGC (Seq. ID No.: 1) is shown in FIG. 5. The experiment was carried out under the following conditions: column: monolithic poly (styrene/divinylbenzene), 60×0.2 mm i.d.; mobile phase: (A) 25 mM TEAB, pH 8.4, (B) 25 mM TEAB, pH 8.4, 20% acetonitrile; linear gradient: 5-50% B in 10 min; flow rate: 3.0 µl/min; temperature: 50° C.; scan: 420-2000 amu; electrospray voltage: 3.40 kV; sheath gas: 40 units; sheath liquid: acetonitrile, 3.0 µl/min; product ions of m/z 1542.5 (charge state: 4-); 4.0 amu isolation width; 35% relative collision energy; sample: 222 ng of the 20 mer. The mass spectroscopic data (m/z, I %) obtained in this manner are then used as an input for the comparative sequencing algorithm. The sequence GACAGGAAAG ACATTCTGGC (Seq. ID No.: 2) which contained an A instead of a T at position 13 was used as the reference sequence. Table 1 summarizes the m/z values of the a, a-B, w and w-B fragment ions for the charge states 1- to 4- that were calculated on the basis of the fragmentation mechanisms described above. The matrix of the FS values was then calculated as outlined in the previous section. In order to make it easier to visualize the result, the matrix was shown in the form of a diagram in which the FS values of the individual bases represented by the letters A, T, G and C were plotted versus the position in the oligodeoxynucleotide sequence. FIG. 6a shows that the reference sequence yielded the best correspondence for the first 6 bases but from position 7 onwards the FS values for other bases had a better match. Especially exchanging T for A resulted in significantly lower values for fitness which strongly indicated an A to T mutation. The exact position of the mutation resulted from the minimum of the FS values clearly identifying an A to T mutation at position 13. The base sequence obtained in this manner (GACAGGAAAGACTTTCTGGC) (Seq. ID No.: 1) completely agrees with the theoretical base sequence (GACAGGAAAG ACTTTCTGGC) (Seq. ID No.: 1). If this sequence is now used as a reference sequence in the algorithm together with the mass spectrometric data from FIG. 5, this results in FIG. 6b. As expected the reference sequence results in the smallest FS value over the entire sequence. The diagram obviously confirms the identity of the reference sequence and thus the sequence of the examined oligodeoxynucleotide. These two examples demonstrate that this method can be used to check the identity of an unknown sequence with a reference sequence as well as to detect point mutations in comparison to a known reference sequence.

Example 2

Sequencing of a 51 mer oligodeoxynucleotide

Figure 7:
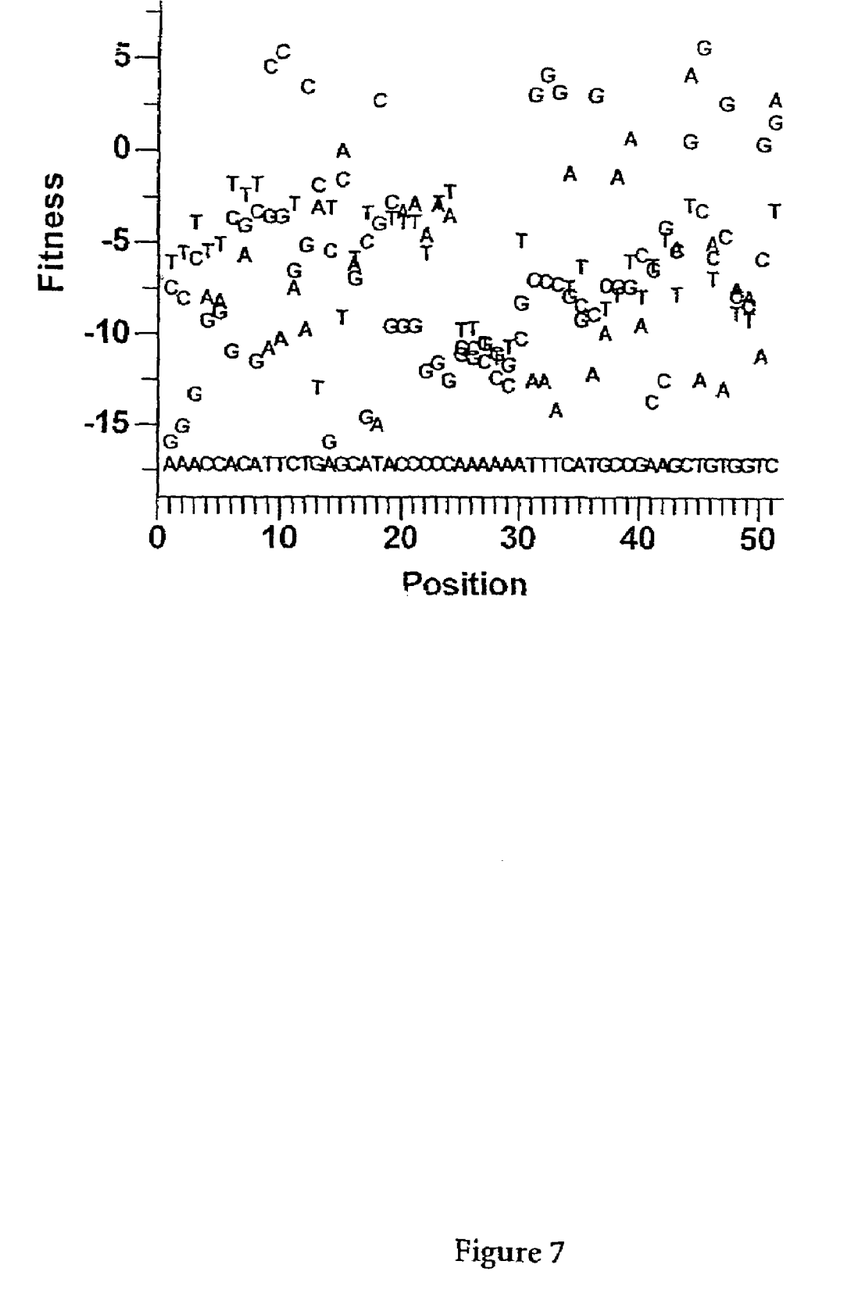
FIG. 7 concerns the sequencing of a 51 mer oligodeoxynucleotide.

An interesting field of application for comparative sequencing is the detection of sequence variants in genomic DNA segments that have been amplified by means of the polymerase chain reaction (PCR). This amplification reaction consists of three steps that are repeated in cycles in which, after denaturation of the DNA double helix into single strands, two different oligodeoxynucleotides of a certain sequence, the so-called primers, are hybridized to specific, complementary sites in order to be subsequently extended to again form the double strands in an enzyme-catalysed polymerization reaction. The segment of the genomic DNA that is to be amplified is delimited by the two primers. Since PCR primers normally have a length of about 20 deoxynucleotides, an amplified PCR product must have a length of more than 40 base pairs in order to contain relevant sequence information. Hence we selected a 51 mer in order to demonstrate that it is possible to check the identity of relatively long DNA molecules. For this a 51 mer (molecular mass: 15580.0) having the sequence AAACCACATT CTGAGCATAC CCCCAAAAAA TTTCATGCCG AAGCTGTGGT C (Seq. ID No.: 3) was fragmented and measured. The experiment was carried out under the following conditions: column monolithic (poly(styrene/divinylbenzene) 60×0.2 mm i.d.; mobile phase: (A) 25 mM butyldimethyl-ammonium bicarbonate, pH 8.4, (B) 25 mM butyldimethylammonium bicarbonate, pH 8.4, 40% acetonitrile; linear gradient: 5-70% B in 10 min: flow rate: 2.0 µl/min; temperature: 50° C., scan: 470-2000 amu; electrospray voltage: 3.40 kV; sheath gas: 40 units; sheath liquid: acetonitrile, 3.0 µl/min; product ions m/z 1729.7 (charge state: 9-); 4.0 amu isolation width; 17% relative collision energy; sample: 635 ng of the 51 mer. The measured MS/MS spectrum was compared with the reference sequence and unequivocally identified as correct on the basis of the fitness values (FIG. 7).

Example 3

Investigation of the Sequence of an 80 mer oligodeoxynucleotide

Figure 8:
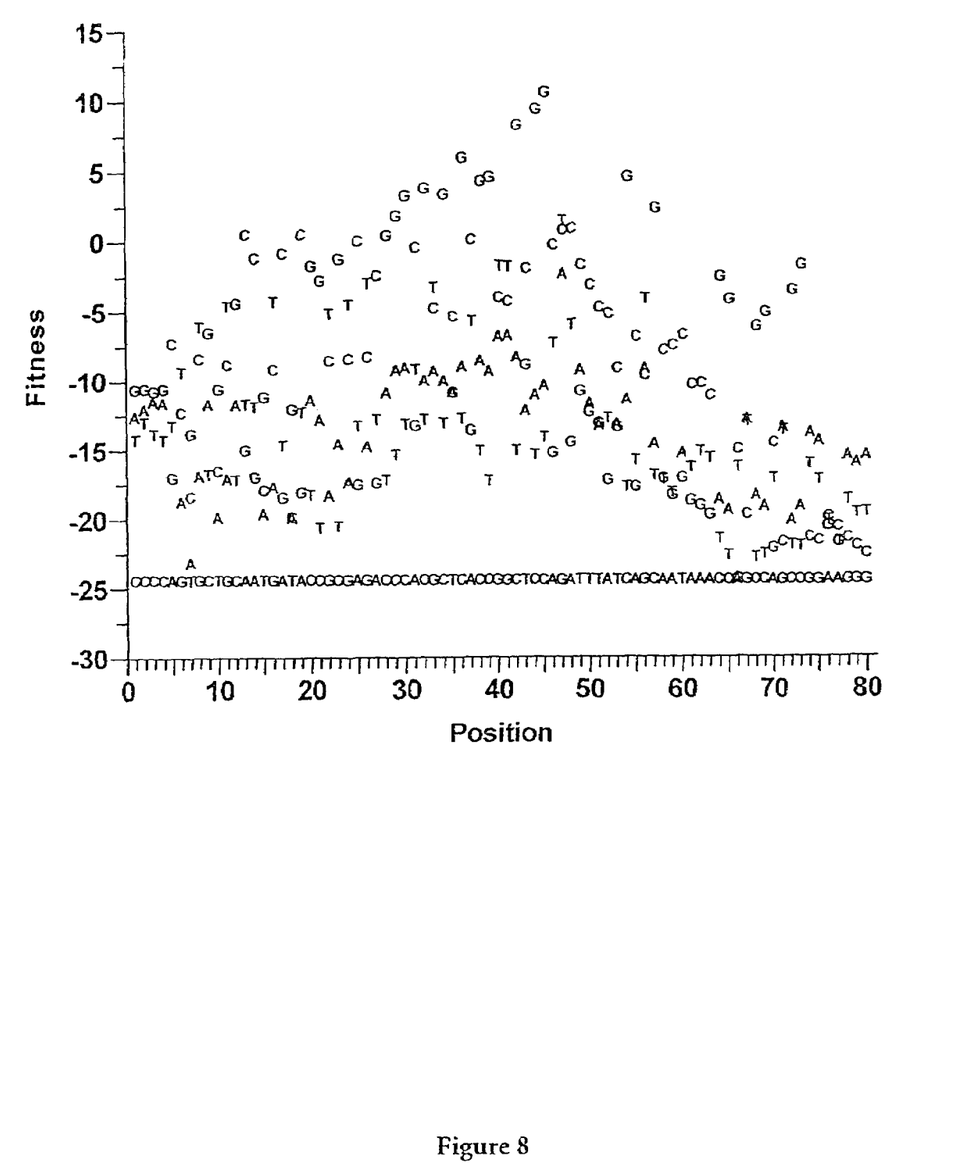
FIG. 8 concerns the examination of the sequence of an 80 mer oligodeoxynucleotide.

Another example which is intended to demonstrate the applicability of the algorithm to identifying long oligonucleotides is shown in FIG. 8. In this case the correctness of the sequence of an 80 mer was checked by comparison with the MS/MS spectrum (CCCCAGTGCT GCAATGATAC CGC-GAGACCC ACGCTCACCG GCTCCAGATT TATCAG-CAAT AAACCAGCCA GCCGGAAGGG) (Seq. ID No.: 4). The experiment was carried out under the following conditions: column: monolithic poly(styrene/divinylbenzene) 60×0.2 mm i.d.; mobile phase: (A) 25 mM butyldimethyl-ammonium bicarbonate, pH 8.4, (B) 25 mM butyldimethylammonium bicarbonate, pH 8.4, 40% acetonitrile; linear gradient: 10-70% B in 10 min; flow rate: 2.0 µl/min; temperature: 70° C.; scan: 470-2000 amu; electrospray voltage: 5.0 kV; sheath gas: 100 units; sheath liquid: acetonitrile, 3.0 µl/min; product ions of m/z 1065.4 (charge state: 23-); 4.0 amu isolation width; 17% relative collision energy; sample: 478 ng of the 80 mer. It turned out that the FS value for the reference sequence always had the smallest value compared to all mutated sequences. Thus the identity of the assumed sequence was unequivocally proven (FIG. 8).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 1

Calculated m/z values of the charge states 1- to 4- of the a, a-B, w and w-B fragment ions of the reference sequence GACAGGAAAGACATTCTGGC (Seq. ID NO.: 2).

| Typ | Charge state | | | |
|---|---|---|---|---|
| | −1 | −2 | −3 | −4 |
| a1-B1 | 97.04 | 48.02 | 31.68 | 23.51 |
| w1-B20 | 195.01 | 97.01 | 64.34 | 48.00 |
| a1 | 248.09 | 123.55 | 82.03 | 61.27 |
| w1 | 306.06 | 152.53 | 101.35 | 75.77 |
| a2-B2 | 426.09 | 212.55 | 141.36 | 105.77 |
| w2-B19 | 484.06 | 241.53 | 160.69 | 120.27 |
| a2 | 561.14 | 280.07 | 186.38 | 139.54 |
| w2 | 635.11 | 317.06 | 211.04 | 158.03 |
| a3-B3 | 739.15 | 369.08 | 245.72 | 184.04 |
| w3-B18 | 813.11 | 406.06 | 270.37 | 202.53 |
| a3 | 850.19 | 424.60 | 282.73 | 211.80 |
| w3 | 964.16 | 481.58 | 320.72 | 240.29 |
| a4-B4 | 1028.19 | 513.60 | 342.06 | 256.30 |
| w4-B17 | 1142.16 | 570.58 | 380.05 | 284.79 |
| a4 | 1163.25 | 581.13 | 387.08 | 290.06 |
| w4 | 1268.21 | 633.61 | 422.07 | 316.30 |
| a5-B5 | 1341.25 | 670.13 | 446.42 | 334.56 |
| w5-B16 | 1446.21 | 722.61 | 481.40 | 360.80 |
| a5 | 1492.30 | 745.65 | 496.77 | 372.33 |
| w5 | 1557.25 | 778.13 | 518.42 | 388.56 |
| a6-B6 | 1670.30 | 834.65 | 556.10 | 416.83 |
| w6-B15 | 1735.26 | 867.13 | 577.75 | 433.07 |
| a6 | 1821.35 | 910.18 | 606.45 | 454.59 |
| w6 | 1861.30 | 930.15 | 619.77 | 464.58 |
| a7-B7 | 1999.35 | 999.18 | 665.78 | 499.09 |
| w7-B14 | 2039.30 | 1019.15 | 679.10 | 509.08 |
| a7 | 2134.41 | 1066.71 | 710.80 | 532.85 |
| w7 | 2165.34 | 1082.17 | 721.11 | 540.59 |
| a8-B8 | 2312.41 | 1155.71 | 770.14 | 577.35 |
| w8-B13 | 2343.35 | 1171.18 | 780.45 | 585.09 |
| a8 | 2447.47 | 1223.24 | 815.16 | 611.12 |
| w8 | 2478.40 | 1238.70 | 825.47 | 618.85 |
| a9-B9 | 2625.47 | 1312.24 | 874.49 | 655.62 |
| a9-B12 | 2656.40 | 1327.70 | 884.80 | 663.35 |
| a9 | 2760.52 | 1379.76 | 919.51 | 689.38 |
| w9 | 2767.45 | 1383.23 | 921.82 | 691.11 |
| a10-B10 | 2938.53 | 1468.77 | 978.84 | 733.88 |
| w10-B11 | 2945.45 | 1472.23 | 981.15 | 735.61 |
| w10 | 3080.51 | 1539.76 | 1026.17 | 769.38 |
| a10 | 3089.58 | 1544.29 | 1029.19 | 771.65 |
| w11-B10 | 3258.51 | 1628.76 | 1085.50 | 813.88 |
| a11-B11 | 3267.58 | 1633.29 | 1088.53 | 816.15 |
| a11 | 3402.63 | 1700.82 | 1133.54 | 849.91 |
| w11 | 3409.56 | 1704.28 | 1135.85 | 851.64 |
| a12-B12 | 3580.64 | 1789.82 | 1192.88 | 894.41 |
| w12-B9 | 3587.56 | 1793.28 | 1195.19 | 896.14 |
| a12 | 3691.68 | 1845.34 | 1229.89 | 922.17 |
| w12 | 3722.62 | 1860.81 | 1240.21 | 929.91 |
| a13-B13 | 3869.68 | 1934.34 | 1289.23 | 966.67 |
| w13-B8 | 3900.62 | 1949.81 | 1299.54 | 974.41 |
| a13 | 4004.74 | 2001.87 | 1334.25 | 1000.44 |
| w13 | 4035.67 | 2017.34 | 1344.56 | 1008.17 |
| a14-B14 | 4182.74 | 2090.87 | 1393.58 | 1044.94 |
| w14-B7 | 4213.68 | 2106.34 | 1403.89 | 1052.67 |
| a14 | 4308.78 | 2153.89 | 1435.59 | 1076.45 |
| w14 | 4348.73 | 2173.87 | 1448.91 | 1086.43 |
| a15-B15 | 4486.79 | 2242.90 | 1494.93 | 1120.95 |
| w15-B6 | 4526.73 | 2262.87 | 1508.24 | 1130.93 |
| a15 | 4612.83 | 2305.92 | 1536.94 | 1152.46 |
| w15 | 4677.78 | 2338.39 | 1558.59 | 1168.70 |
| a16-B16 | 4790.83 | 2394.92 | 1596.28 | 1196.96 |
| w16-B5 | 4855.79 | 2427.40 | 1617.93 | 1213.20 |
| a16 | 4901.87 | 2450.44 | 1633.29 | 1224.72 |
| w16 | 5006.83 | 2502.92 | 1668.28 | 1250.96 |
| a17-B17 | 5079.88 | 2539.44 | 1692.63 | 1269.22 |
| w17-B4 | 5184.84 | 2591.92 | 1727.61 | 1295.46 |
| a17 | 5205.92 | 2602.46 | 1734.64 | 1300.73 |
| w17 | 5319.89 | 2659.45 | 1772.63 | 1329.22 |
| a18-B18 | 5383.92 | 2691.46 | 1793.97 | 1345.23 |
| w18-B3 | 5497.89 | 2748.45 | 1831.96 | 1373.72 |
| a18 | 5534.97 | 2766.99 | 1844.32 | 1382.99 |
| w18 | 5608.94 | 2803.97 | 1868.98 | 1401.89 |
| a19-B19 | 5712.98 | 2855.99 | 1903.66 | 1427.50 |
| w19-B2 | 5786.94 | 2892.97 | 1928.31 | 1445.99 |
| a19 | 5864.02 | 2931.51 | 1954.01 | 1465.26 |
| w19 | 5922.00 | 2960.50 | 1973.33 | 1479.75 |
| [M] | 6171.08 | 3085.04 | 2056.36 | 1542.02 |

What is claimed is:

1. A method for sequencing a nucleic acid, comprising:
   a. measuring a CID spectrum for said nucleic acid using a spectrometer to create a measured CID spectrum;
   b. providing a reference sequence of said nucleic acid;
   c. calculating a CID spectrum for said reference sequence;
   d. comparing the values of said CID spectrum for said reference sequence with the values of said measured CID spectrum;
   e. determining the degree of correspondence between said measured CID spectrum and said calculated CID spectrum to generate a fitness value;
   f. for each position of said reference sequence
      i. replacing the nucleotide at the position in said reference sequence with a different nucleotide selected from the group consisting of A, C, G, and T;
      ii. repeating steps c), d) and e);
      iii. comparing said fitness value generated in step e) to that of the reference sequence to identify the lower fitness value;
      iv. repeating steps i), ii) and iii) with the remaining different nucleotides;
      v. comparing the fitness values to identify the lowest fitness value at said position, thereby determining the identity of the nucleotide at that position; and
   g. selecting for each position the nucleotide having the lowest fitness value, and
   h. generating a user-readable output comprising the sequence of nucleotides selected in step g.

2. The method of claim 1, wherein said fitness value is $$FS = 1/K \cdot \Sigma |100 \cdot \Delta/I\,\%| - b \cdot K + 0.1 \cdot M, \text{ where}$$

K=number of fragment ions that could be assigned a calculated m/z value;

M=number of non-covered a and w positions;

$\Delta$=tolerance value

I=relative intensity b=a coefficient equal to MF/K, where $$MF = 1/K \cdot \Sigma (100 \cdot \Delta/I\,\%).$$

* * * * *